United States Patent [19]
Cottrell

[11] Patent Number: 4,750,938
[45] Date of Patent: Jun. 14, 1988

[54] AQUEOUS PHOSPHATE PIGMENT DISPERSIONS

[75] Inventor: Clark E. Cottrell, Rockaway, N.J.

[73] Assignee: Crompton & Knowles Corporation, New York, N.Y.

[21] Appl. No.: 930,322

[22] Filed: Nov. 12, 1986

[51] Int. Cl.⁴ .................... C08L 1/00; C08L 5/00; C08L 89/00
[52] U.S. Cl. .................... 106/135; 106/137; 106/177; 106/189; 106/193 J; 106/203; 106/209; 106/308 B; 427/3
[58] Field of Search .................... 106/177, 308 B, 135, 106/137, 189, 209, 203, 193 J; 427/3

[56] References Cited

U.S. PATENT DOCUMENTS

| 2,260,871 | 10/1941 | Sawyer et al. | 106/308 B |
| 2,592,305 | 4/1952 | Malm et al. | 106/177 |
| 3,869,546 | 3/1975 | Lund | 424/88 |
| 3,981,984 | 9/1976 | Signorino | 106/193 J |
| 4,636,261 | 1/1987 | Heinze | 106/289 |
| 4,652,313 | 3/1987 | Den Boer et al. | 106/308 L |

Primary Examiner—Theodore Morris

[57] ABSTRACT

This invention relates to a aqueous phosphate pigment dispersion usable for sugar or film coating tablets and the like, comprising like pigment particles, a polymeric colloid, a phosphate viscosity lowering agent which permits a higher concentration of pigment particles in the pigment suspension, and an aqueous solvent. A typical pigment suspension comprises FD&C pigment, a natural gum as the polymeric colloid, a polyphosphate as the viscosity lowering agent and water as the aqueous solvent.

16 Claims, No Drawings

AQUEOUS PHOSPHATE PIGMENT DISPERSIONS

THE BACKGROUND OF THE INVENTION

Pigment suspensions are used for producing coating suspensions for coating such items as pharmaceutial tablets or pills, confectionary pieces, and the like. The pigment suspension is typically stirred into a larger volume of solution to produce a coating suspension which is used in the coating process. One process of coating is generally known as film coating in which the coating solution includes a film forming polymer. U.S. Pat. No. 2,954,323 to Endicott et al. discloses examples of film coating. Another technique, frequently used, with respect to confectionary pieces, is generally known as sugar coating, in which the pigment suspension is added to a sugar syrup solution of sugar and water.

Pigment suspensions for use in making coating suspensions are preferably sold having a concentration of pigment as high as possible. However, as the concentration of pigment increases, the suspension becomes more viscous and tends to reach a point where it becomes difficult to pour from its container. Over time, a thick suspension of pigment may even harden to the extent of becoming unusable.

In developing a high concentration pigment suspension, it is desirable to obtain a product in which the pigment particles form a stable suspension and will not settle. The need is for a pigment suspension which will readily pour from its container and will maintain its uniform properties during both transportation and storage, until ready for application in a coating suspension.

U.S. Pat. No. 3,981,984 to Signorino discloses a pigment suspension which claims to achieve a high concentration of pigment in a non-aqueous solvent. This pigment suspension consists of pigment particles, a protective colloid such as hydroxypropyl cellulose, and a non-aqueous solvent such as ethanol. Signorino discloses that as the pigment particles are added to the solvent, the mixture becomes too viscous, and the further addition of the protective colloid serves to suspend the particles and reduce the viscosity.

In view of the increasingly strict requirements of governmental regulating agencies in regard to the use of organic solvents, it has become desirable to obtain an aqueous pigment suspension. A high content of pigment is not normally possible and the present invention involved a search for a combination of ingredients which would permit a high content of pigment particles in an aqueous suspension. However, the invention is also applicable to suspensions in organic solvents which include a sufficient amount of water to dissolve what is referred to below as the viscosity reducing agent.

THE OBJECTS OF THE INVENTION

One object of the present invention is to achieve a pigment suspension which contains a high pigment content.

Another object of the present invention is to achieve a high concentration pigment suspension in an aqueous solution, or a mixture of water and an organic solvent, or a mixture of water and sugar.

A further object of the invention is to obtain a high concentration pigment suspension which pours readily from its container.

A further object of the invention is to obtain a high concentration pigment suspension which does not settle upon standing, or if settling occurs is easily redispersed.

A further object of the present invention is to obtain a pigment suspension with a high pigment concentration which is capable of being transported to customers in containers, and which may readily be combined with a film-forming polymer solution or sugar solution by stirring.

The above and other objects of the present invention will become apparent from a reading of the following detailed description of the invention and the preferred embodiments thereof.

DETAILED DESCRIPTION OF THE INVENTION

The pigment suspension of the present invention is a mixture of a pigment, a polymeric colloid where necessary for suspension, a viscosity lowering agent, and vechicles which may included water, mixtures of water and sugar (sugar syrup) and mixtures of water and organic solvents.

The pigments suitable for use in the context of the present invention include natural pigments, such as carotenoids, titanium dioxide, iron oxide; FD&C and D&C lakes, and carmine, which are dyes combined with a metal hydroxide substratum. A variety of lakes, including lakes incorporating azo, triphenylmethane, fluorescein, and sulfonated indigo dyes, are suitable in the present invention. FD&C lakes are suitable for application in food, drug, and cosmetic products.

The concentration of pigment in the pigment suspension by weight is in the range of 20% to 70%. Preferably a range of 25% to 45% is obtained. However, the amount of pigment acheived in any particular suspension depends to some degree on the particular pigment used and, somewhat higher contents of one particular pigment or a particular brand of pigment may be achieved than with another.

The polymeric colloid assists in preventing settling and hardening of the pigment. Gums, both natural and synthetic, have been found to be suitable polymeric colloids. Suitable gums include, but are not limited to, gum arabic, quar gum, gum tragacanth, gelatin, citrus pectin, and carrageenan. Preferable gums include gum arabic, xanthan gum and quar gum. The most preferable polymeric colloid is xanthan gum. In substitution of gum, such polymeric colloids as corn starch or polyvinylpyrrolidone may also be employed.

The viscosity lowering agent is a phosphate. In general, phosphates fall into two categories:
(a) Orthophosphates which are phosphoric acid neutralized to varying degrees, and
(b) Polyphosphates (pyrophosphates) which are orthophosphates heated to polymerize the individual phosphate groups.

Orthophosphates are the best buffering agents depending on the degree and type of cationic substitution. Polyphosphates are the only phosphates with sequestering power; long chains for calcium and magnesium, and short chains for heavy metals. In addition, both types exhibit polyvalent anionic character which enables these to bind water to positively charged sites such as proteins. As will be demonstrated in the specific examples these properties are insufficient in themselves to explain the dramatic viscosity lowering effect of certain phosphates.

The presence of one of the viscosity lowering agents can result in a dramatic lowering of the viscosity of the suspension. Consequently, good flowability of the suspension is obtained. The suspension can be readily poured from its container and it neither unduly thickens nor settles. The viscosity lowering agent is present in an amount of 0.005 to 5 percent by weight in the mixture. Preferably, the agent is present in an amount of 0.01 to 3.0 percent. In many cases, even a relatively small amount of agent can drastically and favorably effect the properties of the suspension.

The phosphates which are the subject of the invention are preferably but not limited to, the sodium or potassium salts of polyphosphates. Although all phosphates exhibit a degree of anionic character, orthophosphates (1 phosphate unit) and pyrophosphates (2 units), do not exhibit the stable, viscosity lowering effect observable with polyphosphates (greater than 2 units, commonly available with average chain lengths of 6, 13 and 21 units). This may be because polyphosphates provide steric as well as electrolytic stability. They may, however, be combined with other phosphates to take advantage of special attributes (e.g. buffering).

The above described components are dispersed in an aqueous solution. The amount of water is suitably as high as 60-80 percent, depending on the amount of pigment. As described in greater detail below, organic solvents or sugar may also be included, in which case the amount of water may suitably be in the range of 5 to 30 percent.

Such dispersions, either with or without a percentage of organic solvent, may also be used to color not only the exterior coating of a tablet or confection but also the body of the product as well. The water portion of the formulation provides a solvent for such additives as FD&C soluble dyes where it becomes desirable to combine them with aluminum lakes. The viscosity reducing agent maintains such mixed systems in a stable, fluid state. This enables them to be mixed with product in the case of confections, or further processed as in the wet granulation of solid dosage forms.

EXAMPLE 1

For sugar pan coating of confections, aluminum lakes are mechanically dispersed in 50-70% sugar syrup to form a stable fluid concentrate in which the lake particles are deagglomerated to insure smooth and uniform color coatings. At most, 15-25% pigment may be dispersed in the syrup concentrate depending on sugar content and type of pigment. In general, aluminum lakes must be used at lower levels than other pigments to maintain fluidity.

If polyvinylpyrrolidone is added at a level of less than 2% (higher levels cause thickening), a pigment content of 30% may be achieved depending on the type of pigment. However, if concentrates so prepared are subjected to elevated temperatures, as are occasionally encountered in shipping and storage, they often solidify and become commercially unusable. Thus the consistency of dispersions formulated with varying types and amounts of pigments and stabilizers' and then subjected to accelerated shelf-life tests at elevated temperatures, provides an excellent indicator of one commercial benefit (stability) imparted by the additive which is the subject of the invention.

In addition, such dispersions must be shown to perform at least as well as alternative formulations when diluted for use in the intended application (confectionary coating).

To test whether the phosphates
(a) stabilize commercial high-pigment sugar dispersions under adverse conditions, and
(b) perform the intended coating function,
a commercial lime-green sugar-based color dispersions was prepared in three versions with 1.0% polyvinylpyrrolidone. 0.4% and 0.5% Sodium Hexametaphosphate respectively (See Formulations).

During the course of shelf-life testing the PVP stabilized dispersion remained fluid but became visibly thicker at room temperature while becoming unpourable within days at 60° C. The phosphate-stabilized dispersions remain fluid at all temperatures and concentrations tested for at least one month (1 month at 60° C. equivalent to approximately 6 mo-1yr at room temperature). Thus phosphates provide the benefit of increased stability over state-of-the-art stabilizers.

When the dispersions were coated (15 applications at a dilution of 1:15 in 70% sugar syrup) in parallel, phosphate dispersions gave an even and uniform coating after 10 applications and resulted is a confection product whose appearance was of an equally high quality as the control.

Thus phosphates provide a superior means to stabilize color dispersion, while maintaining a performance level equal to or better than state of the art products.

| Ingredient | I | II | III |
| --- | --- | --- | --- |
| Water | 29.4 | 30.0 | 29.9 |
| Sugar | 43.4 | 43.4 | 43.4 |
| Sodium Benzoate | .2 | .2 | .2 |
| FD&C Yellow #5 Alum. Lake | 8.5 | 8.5 | 8.5 |
| FD&C Blue #1 Alum. Lake | 8.5 | 8.5 | 8.5 |
| Titanium Dioxide | 9.0 | 9.0 | 9.0 |
| Polyvinylpyrrolidone | 1.0 | — | — |
| Sodium Hexametaphosphate | — | 0.4 | 0.5 |

EXAMPLE 2

In the coating of pharmaceuticals, sugar coating has been replaced largely by film coating primarily for reasons of consistency and economy (time consumption). Initially this was done by dissolving a film former such as modified cellulose polymer in an organic solvent, suspending pigment (pigment concentrates) in the solution and spraying the suspension onto a tumbling bed of tablets while evaporating the solvent with a stream of warm air. As tablet pans became more thermodynamically efficient, water was substituted for organic solvents which mainly consisted of a mixture of alcohol and methylene chloride (to reduce the flash point). This substitution reduced the danger of fire, the loss of expensive solvent and risk of exposure to carcinogens. It became apparent that the most economical and compatible vehicle for suspending the color concentrate for further dilution in the aqueous coating suspension was water. However, additives were needed which would disperse levels of pigment above 20% and maintain the dispersion once achieved. By combining polyphosphates with common thickening agents (see attached formula) a fluid, high-pigment, commercially useful color concentrate can be achieved with a viscosity much below that obtained without the aid of a dispersant (1225-1515 cps vs. 3850 cps without phosphate).

When aqueous pigment dispersions formulated with low Titanium Dioxide content (and hence lower pH's) are subjected to heat in storage tests, they do not exhibit the necessary long-term stability (6 mo.-1 year). This is believed to be due to the tendency of polyphosphates to hydrolyze in aqueous media especially when subjected to heat and acidity. Consequently, such dispersions were reformulated with both monophosphates (disodium phosphate) and longer chain length Sodium Hexametaphosphates to maintain high pH and equilibrium in favor of the unhydrolyzed form. It can be seen from the viscosity data collected in the following table that by using combinations of phosphates it is possible to formulate aqueous dispersions with a shelf-life equivalent to 6 months-1 year while maintaining the benefits of compatibility and economy. These systems also reduce the amount of incidentally introduced plasticizer used as a vehicle in conventional aqueous-miscible color dispersions which can adversely affect drying time and film characteristics.

| Base - Example 2 | |
| --- | --- |
| H₂O | 63.8 |
| Xanthan Gum | .1 |
| Potassium Sorbate | .1 |
| Methyl Paraben | .1 |
| Propyl Paraben | .1 |
| Propylene Glycol (retardant for gum) | 2.0 |
| Red #40 AL-39% | 9.0 |
| Yellow #5 AL-36% | 17.3 |
| Titanium Dioxide | 6.7 |
| | 100.00 |
| Total Pigment 30.00% | |

| | Key to Sample Designation | | |
| --- | --- | --- | --- |
| Designation | Sodium Hexameta Phosphate Conc. (Chain Length 13) | Sodium Hexameta Phosphate Conc. (Chain Length 21) | Disodium Phosphate (Chain Length 1) |
| 1.4 | 0.4% | — | — |
| 1.10 | 1.0 | — | — |
| 2A.4 | 0.4 | 0.2% | — |
| 2A.10 | 1.0 | 0.5% | — |
| 2B.4 | 0.4 | — | 0.2% |
| 2B.10 | 1.0 | — | 0.5 |
| 3.4 | 0.4 | 0.2 | 0.2 |
| 3.10 | 1.0 | 0.5 | 0.5 |
| Control 1 (Base) | — | — | — |
| C 2 | — | 0.5 | — |
| C 3 | — | — | 0.5 |
| C 4 | — | 0.5 | 0.5 |

| Results of Accelerated Shelf-Life Tests (60° C.) with Various Phosphate Additions. | | | | | | |
| --- | --- | --- | --- | --- | --- | --- |
| | T = 0 | | T = 21d | | T = 30d | |
| Designation | Viscosity | pH | Viscosity | pH | Viscosity | pH |
| 1.4 | 1375 cps | 5.4 | Solid | — | — | — |
| 1.10 | 1290 | 5.7 | Solid | — | — | — |
| 2A.4 | 1520 | 5.5 | Solid | — | — | — |
| 2A.10 | 1480 | 5.8 | 1875 cps | 5.5 | 1750 | 5.5 |
| 2B.4 | 800 | 5.6 | Solid | — | — | — |
| 2B.10 | 1275 | 6.0 | 1220 | 5.7 | Paste | 5.7 |
| 3.4 | 1040 | 5.7 | Solid | — | — | — |
| 3.10 | 1340 | 6.2 | 2170 | 5.7 | 3150 | — |
| C 1 (Base) | 3850 | 4.8 | Solid | — | — | — |
| C 2 | 1295 | 5.4 | Solid | — | — | — |
| C 3 | 410 | 5.7 | Solid | — | — | — |
| C 4 | 950 | 5.9 | Solid | — | — | — |

NOTE:
Control 1 (No Phosphates) Solid at RT after 14d.

EXAMPLE 3

Phosphates are known for their buffering properties and their ability to alter proteins to increase their emulsifying capacity and their sequestering (meaning the formation of a soluble complex with soluble cations) qualities. When they are used in this last capacity, to prevent the gelation of gums by contaminating cations, they are extremely effective at low concentrations (as in U.S. Pat. No. 3,663,284 Marine Colloids). However, when insoluble Aluminum Lakes are present in any amount and the concentration of polyphosphates is raised, a dramatic decrease in viscosity (as observed in Example 1 & 2) occurs which cannot be explained by the 3 functional properties listed above. To delineate these differences in mechanism, the following experiment was performed.

Slurries containing 21% Aluminum Lakes with and without 0.5% Sodium hexametaphosphate were centrifuged and supernate and pellet were subjected to atomic absorption spectroscopy to determine the presence of aluminum, phosphorus and sodium. The following partition was observed:

| | Water | Aluminum | Phosphorus | Sodium |
| --- | --- | --- | --- | --- |
| Control Slurry | | | | |
| Supernate | 65% | Trace | — | 50%[1] |
| Pellet | 35% | 100% | — | 50% |
| Phosphate Slurry | | | | |
| Supernate | 64% | Trace | 0% | 46% |
| Pellet | 36% | 100% | 100% | 54% |

[1]Residual Na+ from laking process.

It is evident that the phosphate is binding tightly to the insoluble Aluminum Lake particle and not chelating the trace of aluminum ion present in the supernate.

Sodium on the other hand is partially ionized and partially bound either directly to the surface of the particle or indirectly to it through the phosphate backbone. The increasingly lower solubility constants for the secondary, etc. sodium atoms on the phosphate chain would indicate the latter mechanism.

Further indirect evidence for the nature of the reaction of phosphates with Aluminum Lake particles lies in the observation that the FD&C dyes which are bound to the lake during the laking process are displaced by the phosphate and appear as water soluble "bleed".

When 50% titanium dioxide slurries are subjected to the same experiment, phosphate and sodium quantitatively partition just as the water does indicating that the phosphate is not at all or much less strongly bound to the particle. Indeed in certain high pigment (GT 65%) titanium dioxide slurries the presence of this phosphate salt causes a marked viscosity increase (instead of a decrease) as is demonstrated in the following example.

This data confirms that phosphates react with different particles via different mechanisms and that the reaction with Aluminum Lake particles is unique in comparison to what was previously known (U.S. Pat. No. 3,663,284).

EXAMPLE 4

Aqueous slurries containing 70% titanium dioxide (Pharmaceutical or Food Grade $TiO_2$ as required for coating tablets or confections) were mechanically dispersed as in U.S. Pat. No. 3,884,871. These were treated as shown in the following table, examined microscopically and held overnight at room temperature for observation on the following day.

|  |  | Initial Dispersion | Consistency after 24 h |
|---|---|---|---|
| I. | Control (no additives) | few agglomerates, fair spreadability. | fluid with soft settle |
| II. | 0.2% Sodium Hexametaphosphate | few agglomerates, excellent spreadability. | 90% solidified |
| III. | 0.2% NaCitrate (polycarboxylic acid salt) | few agglomerates, moderately good | 100% solidified spreadability. |

This method of dispersion may be adequate for short-term dispersion (although the control indicates that the same results are achievable using high-shear mixing without additives) until final stabilization is conveyed by the anchored polymer, or when using pre-treated titanium dioxide as is common for paints. However, it is not acceptable for the tablet coating application which is the object of this invention because it shows the opposite effect when permitted raw materials are used or when long-term stability is required.

EXAMPLE 5

While phosphates have a thickening effect on pure $TiO_2$ slurries, they are able to stabilize dispersions consisting mainly of $TiO_2$ with only minimal amounts of Aluminum Lakes. Using the attached formulation (where Aluminum Lakes comprise less than 4% of the total pigment present), a dispersion was prepared mechanically. This dispersion was split into three parts, handled as designated and allowed to equilibrate overnight before testing.

Aliquots were stored at room temperature and at 60° C. for three months with the results as summarized below:

| SAMPLE DESIGNATION | TIME ZERO VISCOSITY | pH | TIME = 3 MONTHS VISCOSITY | pH |
|---|---|---|---|---|
| I. Control | Became totally solid overnight separating into curd and synerisis fluid. |  | Test discontinued. |  |
| II. Control + 0.2% Sodium Hexametaphosphate (NaHMP) | 260 CPS | 8.3 | 325 CPS STABLE at both 21° C. and 60° C. | 8.3 |
| III. Control + 0.2% NaHMP-adjusted to pH = 7.0 with Phosphoric acid. | 255 CPS | 7.0 | 350 CPS STABLE at both 21° C. & 60° C. | 7.0 |

At the end of the test period the sample at neutral pH (III) exhibited a slight color change and was not further tested. Sample II was spray coated under identical conditions against a fresh sample using an aqueous suspension of commercially available plasticized cellulose polymer (3% weight gain). The coating gave comparable results in both performance and tablet appearance.

Thus while the compound which is the subject of the invention does not give stable dispersions using only $TiO_2$, it does confer both stability (independent of pH) and performance in the intended application when this and other pigments are combined with Aluminum Lakes even at low levels. This conveys a distinct commercial advantage since pastel colors are favored in the industry because the high $TiO_2$ content reduces the price of the dispersion and takes advantage of the high light-scattering (hiding) power of $TiO_2$ while still providing a distinctive identifying shade.

| EXAMPLE 5 - BASE | |
|---|---|
| Distilled Water | 62.5% |
| Propylene Glycol | 2.0 |
| Methyl Paraben | 0.1 |
| Propyl Paraben | 0.1 |
| Potassium Sorbate | 0.2 |
| Xanthan Gum | .1 |
| FD&C Yellow #6 Aluminum Lake - 16% | 1.2 |
| Titanium Dioxide | 33.8 |
|  | 100.0% |
| Total Pigment 35.0 | |

EXAMPLE 6

Should it be desirable to use a plasticizer as the vehicle for the dispersion for microbiological or consistency reasons, these may be used at the required level, substituting water for the remainder of the formulation. In such cases, the dispersion benefits from the addition of phosphates as a viscosity control agent as the following examples demonstrate. A typical formulation for a colored coating suspension consists of the following:

|  |  | SOLIDS |
|---|---|---|
| Modified Cellulose Polymer | 10.0% | 10.0 |
| Plasticizer | 3.0% | 3.0 |
| Color (30% Pigment) | 5.0% | 1.5 |
| Dist. Water | 83.0% | — |
|  | 100.0 | |

By removing the plasticizer and the pigment from the above formula, and keeping the pigment at a practical level of 30%, it is possible to formulate a color/plasticizer concentrate as follows:

| DISPERSION FORMULA | | PIGMENT FORMULA | |
|---|---|---|---|
| Plasticizer | 50.0% | FD&C Blue #1 AL(34%) | 33.0% |
| Pigment | 30.0 | FD&C Yellow #5 AL(17%) | 17.0 |
| Remainder (as water) | 20.0 | Titanium Dioxide | 50.0 |

When common plasticizers such as propylene glycol or glycerin are dispersed with and without 0.5% Sodium Hexametaphosphate according to the formula above, the data contained in the table below were obtained after a 24 hour equilibration period:

|  | Control (Viscosity) | With 0.5% NaHMP (Viscosity) |
| --- | --- | --- |
| I. Glycerin | barely fluid/too viscous to measure | 715 cps |
| II. Propylene Glycol | 4135 cps | 3725 cps |

It can be seen from this data that there is sufficient water to permit the phosphate to dissolve and exert its viscosity reducing effect to varying degrees.

Such dispersions are not only valuable for coating tablets but may also be used to internally color the body of confections and the like. In such applications as chewing gum they offer softening and humectant properties, while avoiding the thickening associated with pure glycerin dispersions. In dispersions which are formulated using insoluble lakes to retain color in the chewed bolus, they provide additional solvent for the more concentrated water-soluable dye portion of the formula that is responsible for color intensity.

I claim:

1. A composition consisting essentially of edible ingredients including 20-70% lake pigment, 0.005 to 5% polymeric colloid, 0.005-5% viscosity lowering agent, the viscosity lowering agent being a salt of a polyphosphate or acid thereof, and 5-80% water.

2. The composition of claim 1 wherein the polymeric colloid is a natural or synthetic gum.

3. The composition of claim 1, comprising a gum selected from the group consisting of gum arabic, guar gum, agar, xanthan gum, PG alginate, hydroxypropyl cellulose, gum trag, gelatin, pectin, and carrageenan.

4. The composition of claim 1, wherein the pigment is an FD&C Lake, D&C Lake or carmine.

5. The composition of claim 1, wherein the lake pigment can be combined with other pigments or soluble colors.

6. The composition of claim 1, wherein the viscosity lowering agent is sodium hexametaphosphate, tripolyphosphate or sodium trimetaphosphate.

7. The composition of claim 1, wherein the percent of the pigment is 25 to 45%, 0.01 to 2 percent of a gum, 0.05 to 3 percent of a viscosity lowering agent, and 10 to 75 percent of an aqueous solvent.

8. A composition consisting essentially of 20-70% lake pigment, 0.0050-5% viscosity lowering agent, the viscosity lowering agent being a salt of or a polyphosphate or and thereof, 5-80% aqueous solvent, and 10-70% organic solvent.

9. The composition of claim 8 wherein the aqueous solvent is water and the organic solvent is selected from the group comprising propylene glycol and glycerin.

10. The composition of claim 8 wherein the pigment is an FD&C lake, D&C lake, or carmine.

11. The composition of claim 8 wherein the lake pigment can be combined with other pigments or soluble colors.

12. The composition of claim 8, wherein the viscosity lowering agent is sodium hexametaphosphate, tripolyphosphate or sodium trimetaphosphate.

13. A composition consisting essentially of 20-50% lake pigment, a 0.05-5% viscosity lowering agent, the viscosity lowering agent being a salt of a polyphosphate or acid thereof, 20-50% sugar and 5-60% water.

14. The composition of claim 13, wherein the pigment is an FD&C lake, D&C lake or carmine.

15. The composition of claim 13, wherein the lake pigment can be combined with other pigments or soluble colors.

16. The composition of claim 13, wherein the viscosity lowering agent is sodium hexametaphosphate, tripolyphosphate or sodium trimetyaphosphate, and the sugar is sucrose, sorbitol or fructose.

* * * * *